(12) United States Patent
Slusarewicz

(10) Patent No.: US 10,718,757 B2
(45) Date of Patent: Jul. 21, 2020

(54) METHOD FOR THE RAPID AND CONVENIENT DETECTION AND ENUMERATION OF NEUTROPHILS IN BIOLOGICAL SAMPLES

(71) Applicant: MEP Equine Solutions LLC, Lexington, KY (US)

(72) Inventor: Pawel Slusarewicz, Lexington, KY (US)

(73) Assignee: MEP Equine Solutions LLC, Lexington, KY (US)

(*) Notice: Subject to any disclaimer, the term of this patent is extended or adjusted under 35 U.S.C. 154(b) by 0 days.

(21) Appl. No.: 15/948,732

(22) Filed: Apr. 9, 2018

(65) Prior Publication Data
US 2018/0292392 A1    Oct. 11, 2018

Related U.S. Application Data

(60) Provisional application No. 62/484,014, filed on Apr. 11, 2017.

(51) Int. Cl.
| | |
|---|---|
| G01N 33/50 | (2006.01) |
| G01N 21/64 | (2006.01) |
| G01N 15/06 | (2006.01) |
| G01N 15/14 | (2006.01) |
| G01N 31/22 | (2006.01) |
| G01N 33/04 | (2006.01) |
| G01N 15/10 | (2006.01) |

(52) U.S. Cl.
CPC ......... *G01N 33/5094* (2013.01); *G01N 15/06* (2013.01); *G01N 15/1463* (2013.01); *G01N 21/6428* (2013.01); *G01N 31/22* (2013.01); *G01N 33/04* (2013.01); *G01N 2015/0693* (2013.01); *G01N 2015/1006* (2013.01); *G01N 2015/1486* (2013.01); *G01N 2021/6439* (2013.01)

(58) Field of Classification Search
CPC .......... G01N 33/5094; G01N 15/1463; G01N 15/06; G01N 21/6428; G01N 31/22; G01N 33/04; G01N 2021/6439; G01N 2015/0693; G01N 2015/1006; G01N 2015/1486
See application file for complete search history.

(56) References Cited

U.S. PATENT DOCUMENTS 6,350,613 B1    2/2002   Wardlaw et al.

FOREIGN PATENT DOCUMENTS

WO    WO9202632    2/1992

OTHER PUBLICATIONS

Moloney et al. Esterase activity in leukocytes demonstrated by the use of naphthol AS-D chloroacetate substrate. J Histochem Cytochem (1960), 8, 200-207. (Year: 1960).*
Bass et al. Flow Cytometric Studies of Oxidative Product Formation by Neutrophils: A Graded Response to Membrane Stimulation. The Journal of Immunology (1983), 130, 1910-1917. (Year: 1983).*
L.D. Leder. Diagnostic experiences with the naphthol AS-D chloroacetate esterase reaction. Blut (1970), 21(1), 1-8. (Year: 1970).*
Mambo et al. Primary Malignant Lymphomas of the Breast. Cancer (1977), 39, 2033-2040. (Year: 1977).*
Pascottini et al. Comparison between cytology and histopathology to evaluate subclinical endometritis in dairy cows.Theriogenology (2016), 86, 1550-1556. (Year: 2016).*
Trend et al. Leukocyte Populations in Human Preterm and Term Breast Milk Identified by Multicolour Flow Cytometry. PLoS One (2015), 10(8), e0135580, 17 pages. (Year: 2015).*
Wang et al. A near-infrared fluorescent probe based on chloroacetate modified naphthofluorescein for selectively detecting cysteine/homocysteine and its application in living cells. Photochem. Photobiol. Sci (2016), 15, 1393-1399. (Year: 2016).*
Winkler et al. Parturition at term: parallel increases in interleukin-8 and proteinase concentrations and neutrophil count in the lower uterine segment. Human Reproduction (1999), vol. 14 No. 4 pp. 1096-1100. (Year: 1999).*
Ayres-Silva et al. Sequential morphological characteristics of murine fetal liver hematopoietic microenvironment in Swiss Webster mice. Cell Tissue Res (2011) 344:455-469. (Year: 2011).*
Alhussien et al., "A comparative study on the blood and milk cell counts of healthy, subclinical, and clinical mastitis Karan Fries cows," Vet World, 2015, 8:685-689.
Alhussien,et al., "fucidence of mastitis and activity of milk neutrophils in Tharparkar cows reared under semi-arid conditions." Trop Anim Health Prod, 2016, 48:1291-1295.
APHIS, "Determining U.S. Milk Quality Using Bulk-tank Somatic Cell Counts," USDA, 2011, 1-5.
Arnold et al., "Management of the Dry Cow to Prevent Mastitis," University of Kentucky, 2012, 1-3.
Barbano et al., "nfluence of Milk Somatic Cell Count and Milk Age on Cheese Yield." J Dairy Sci, 1991, 74(2):369-388.
Barkema et al., "Herd level approach to high bulk milk somatic cell count problems in dairy cattle," Vet Q, 2013, 33(2):82-93.
Barnum et al., "The Use of the California Mastitis Test for the Detection of Bovine Mastitis," Can Vet J., 1961, 2(3):83-90.
Baumgart et al., "Fluorescence probe partitioning between Lo/Ld phases in lipid membranes," Biochim Biophys Acta, 2007, 1768:2182-2194.
Beaudeau et al., "Association between milk somatic cell counts up to 400,000 cells/ml and clinical mastitis in French Holstein cows," Vet Rec, 1998, 143(5):685-687.

(Continued)

*Primary Examiner* — Sean C. Barron
(74) *Attorney, Agent, or Firm* — Fish & Richardson P.C.

(57) ABSTRACT

Methods are provided to facilitate the detection and enumeration of neutrophils in bodily fluids, including milk. The methods incorporate the fluorescent staining of neutrophils using fluorogenic enzyme substrates, the imaging of fluorescent cells using a digital device, and the electronic counting of the cells.

Figure 1:
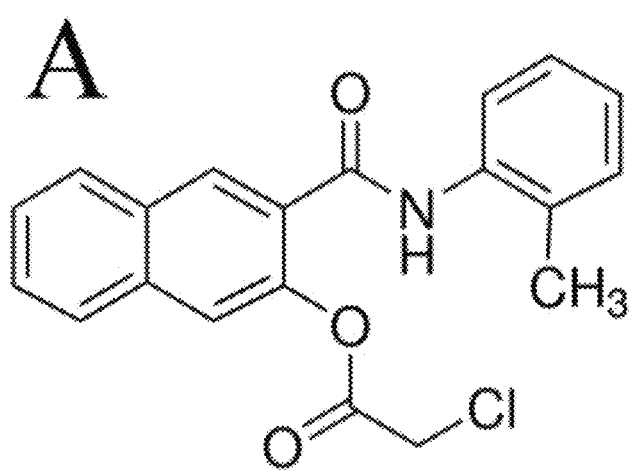
Figure 1:
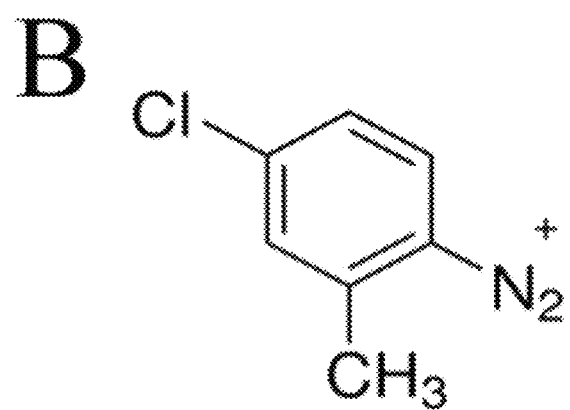

16 Claims, 9 Drawing Sheets
(4 of 9 Drawing Sheet(s) Filed in Color)

(56) References Cited

OTHER PUBLICATIONS

Berghash et al., "Effects of antibiotic treatment of nonlactating dairy cows on antibiotic resistance patterns of bovine mastitis pathogens," Antimicrob Agents Chemother, 1983, 24:771-776.

Berglund et al., "Quarter milking for improved detection of increased SCC," ReprodDomest Anim, 2007, 42:427-432.

Bodoh et al., "Variation in Wisconsin Mastitis Test Scores of bucket milk samples and relationship to bacterial infections," J Daily Sd, 1981, 64:123-129.

Bradley et al., "Bovine mastitis: an evolving disease," Vet J, 2002, 164(2):116-128.

Brazil et al., "Kinetics of pulmonary neutrophil recruitment and clearance in a natural and spontaneously resolving model of airway inflammation," Clin Exp Allergy, 2005, 35:854-865.

Butterfield et al., "The dual roles of neutrophils and macrophages in inflammation: a critical balance between tissue damage and repair," J Athl Train, 2006, 41:457-465.

Cinar et al., "Effect of somatic cell count on milk yield and composition of first and second lactation dairy cow," Ital J Anim Sci, 2015, 14:105-108.

Dohoo et al., "Somatic cell counts in bovine milk," Can Vet J, 1982, 23:119-125.

Dolbeare et al., "Alkaline phosphatase and an acid arylamidase as marker enzymes for normal and transformed WI-38 cells," J Histochem Cytochem, 1980, 28:419-426.

Dosogne et al., "Differential leukocyte count method for bovine low somatic cell count milk," J Dairy Sci, 2003, 86:828-834.

Edmondson et al., "Selective Dry Cow Therapy," Veterinary Practice, 2015, 47:46-50.

Geary et al., "Estimating the impact of somatic cell count on the value of milk utilising parameters obtained from the published literature," J Daily Res, 2014, 81:223-232.

Geary et al., "Meta-analysis to investigate relationships between somatic cell count and raw milk composition, Cheddar cheese processing characteristics and cheese composition," Irish J Agr Food Res, 2013, 52:119-133.

Goncalves et al, "Using milk leukocyte differentials for diagnosis of subclinical bovine mastitis," J Dairy Res, 2017, 84:309-317.

Hagnestam-Nielsen et al., "Relationship between somatic cell count and milk yield in different stages of lactation," J Dairy Sci, 2009, 92:3124-3133.

Halasa et al., "Production loss due to new subclinical mastitis in Dutch dairy cows estimated with a test-day model," J Dai,y Sci, 2009, 92:599-606.

Halasa et al., "Economic effects of bovine mastitis and mastitis management: a review," Vet Q, 2007, 29:18-31.

Hortet et al., "Calculated milk production losses associated with elevated somatic cell counts in dairy cows: review and critical discussion," Vet Res, 1998, 29:497-510.

Dingwell et al., "Evaluation of the California mastitis test to detect an intramammary infection with a major pathogen in early lactation dairy cows," Can Vet J, 2003, 44(5):413-415.

Jaggi et al., "Absorption and fluorescence spectraof disperse red 19—An azo dye," JndJ Pure Appl. Phys, 2013, 51:883-836.

Kashima et al., "Use of chloroacetate esterase staining for the histological diagnosis of prosthetic joint infection," Virchows Arch, 2015, 466:595-601.

Kelly et al., "Correlation between bovine milk somatic cell count and polymorphonuclear leukocyte level for samples of bulk milk and milk from individual cows," J Dairy Sci, 2000, 83:300-304.

Koldeweij et al., "Relation of milk production loss to milk somatic cell count," Acta Vet Scand, 1999, 40:47-56.

Kromker et al., "Mastitis treatment-Reduction in antibiotic usage in dairy cows," Reprod Domest Anim, 2017, 52(Suppl 3):21-29.

Lam et al., "Mastitis diagnostics and performance monitoring: a practical approach," Ir Vet J, 2009, 62(Suppl 4):S34-39.

Li et al., "Role of somatic cells on dairy processes and products: a review," Dairy Sci Technol, 2014, 94:517-538.

Looper et al., "Reducing Somatic Cell Count in Dairy Cattle," University of Arkansas, 2012, 1-4.

Ma et al., "Effects of somatic cell count on quality and shelf-life of pasteurized fluid milk," J Dai,y Sci, 2000, 83:264-274.

Mazal et al., "Effect of somatic cell count on Prato cheese composition," J Dairy Sci, 2007, 90:630-636.

Mehrzad et al., "Viability of milk neutrophils and severity of bovine coliform mastitis," J Daily Sci, 2004, 87:4150-4162.

Mollenhorst et al., "Somatic cell count assessment at the quarter or cow milking level," J Dairy Sci, 2010, 93:3358-3364.

Mungube et al., "Reduced milk production in udder quarters with subclinical mastitis and associated economic losses in crossbred dairy cows in Ethiopia," Trap Anim Health Prod, 2005, 37:503-512.

O'Brien et al., "Abstract #: 365: Milk SCC and PMN as indicators of milk processability and subsequent cheese quality," Presented at Proceedings of the 54$^{th}$ EAAP Annual Meeting, Bled Slovenia, Sep. 5-8, 2004, 6 pages.

Oliver et al., "Antimicrobial resistance of mastitis pathogens," Vet Clin North Am FoodAnim Pract, 2012, 28:165-185.

Osteras et al., "Determinants of success or failure in the elimination of major mastitis pathogens in selective dry cow therapy," J Dairy Sci, 1999, 82:1221-1231.

Ott et al., "Cost of Herd-Level Production Losses Associated with Subclinical Mastitis in U.S. Dairy Cows," Presented at Proceedings of the 38$^{th}$ Annual Meeting of National Mastitis Council, Arlington VA, Feb. 14-16, 1999, 152-153.

Paape et al., Intramammary defense against infections induced by *Escherichia coli* in cows. Am J Vet Res, 1996, 57:477-482.

Paape et al., "Defense of the bovine mammary gland by polymorphonuclear neutrophil leukocytes," J Mammary Gland Biol Neoplasia, 2002, 7(2):109-121.

Parker et al., "Quarter-level analysis of subclinical and clinical mastitis in primiparous heifers following the use of a teat sealant or an injectable antibiotic, or both, precalving," J Daily Sci, 2008, 91:169-181.

Petrovski et al., "A review of the factors affecting the costs of bovine mastitis," JS Afr Vet Assoc, 2008, 77:52-60.

Pillai et al., "Application of differential inflammatory cell count as a tool to monitor udder health," JDairy Sci, 2001, 84:1413-1420.

Rindsig et al., "Complete versus selective dry cow therapy for mastitis control," J Dairy Sci, 1978, 61:1483-1497.

Rivas et al., "Longitudinal evaluation of bovine mammary gland health status by somatic cell counting, flow cytometry, and cytology," J Vet Diagn Invest, 2001. 13:399-407.

Schukken et al., "Monitoring udder health and milk quality using somatic cell counts," Vet Res 2003, 34:579-596.

Schwarz et al., "Flow cytometric differential cell counts in milk for the evaluation of inflammatory reactions in clinically healthy and subclinically infected bovine mammary glands," J Daily Sci, 2011, 94:5033-5044.

Schwarz et al., "Microscopic differential cell counts in milk for the evaluation of inflammatory reactions in clinically healthy and subclinically infected bovine mammary glands," JDairy Res, 2011, 78:448-455.

Schwarz et al., "Somatic cell counts and bacteriological status in quarter foremilk samples of cows in Hesse, Germany—a longitudinal study," J Daily Sci, 2010, 93:5716-5728.

Sharma et al., "Relationship of Somatic Cell Count and Mastitis: An Overview," Asian-Aust J Anim Sci, 2011, 24:429-438.

Sigma-Aldrich, Inc., "Naphthol AS-D Chloroacetate Esterase and a-Naphthyl Acetate Esterase (Procedure No. 90)," 2018, 1-2.

Swain et al., "Neutrophil dynamics in the blood and milk of crossbred cows naturally infected with *Staphylococcus aureus*," 2015, Vet World 8:336-345.

Thurmond et al., "A Method to Estimate the Somatic Cell Count of Milk from a Mastitic Quarter Using Composite Somatic Cell Count," Can J Vet Res, 1990, 54:190-194.

Tsuchiya et al., "The fluorescent simultaneous azo dye technique for demonstration of tartrate-resistant acid phosphatase (TRAP) activity in osteoclast-like multinucleate cells," J Bone Miner Metab, 1995, 13:71-76.

Wozniak et al., "Lysosomal enzyme cytochemistry of blood neutrophils," J Clin Pathol, 1978, 31:648-653.

(56) References Cited

OTHER PUBLICATIONS

Wright et al., "Neutrophil function in inflammation and inflammatory diseases," Rheumatology (Oxford), 2010, 49:1618-1631.
Yam et al., Cytochemical identification of monocytes and granulocytes, Am J Clin Pathol, 1971, 55:283-290.
Ziomek et al., "A highly fluorescent simultaneous azo dye technique for demonstration of nonspecific alkaline phosphatase activity," J Histochem Cytochem, 1990, 38:437-442.

* cited by examiner

METHOD FOR THE RAPID AND CONVENIENT DETECTION AND ENUMERATION OF NEUTROPHILS IN BIOLOGICAL SAMPLES

CLAIM OF PRIORITY

This application claims the benefit of U.S. Provisional Patent Application No. 62/484,014 filed Apr. 11, 2017.

FIELD OF THE INVENTION

This document relates to the diagnosis of inflammatory conditions and describes methods for quantifying the number of neutrophils in body fluids, including milk.

BACKGROUND

The process of inflammation is characterized by the rapid influx of a particular granulocyte, the neutrophil, into the affected area as a response to either physical injury or pathogen invasion[1,2]. Detection of elevated neutrophil levels, therefore, represents a marker for numerous inflammatory events and conditions that can be useful in the diagnosis and subsequent treatment of disease. Three examples of areas in which detection of neutrophils is of clinical value are intra-mammary mastitis in cows and other domesticated herbivores[3], in acute respiratory distress syndrome (ARDS) in humans and in equine inflammatory airway disease (EIAD)[4].

Traditionally neutrophils in tissue or bodily fluids are detected and/or enumerated by either one of two ways. The first is by using manual microscopic examination of samples under high power following cytological staining (such as hematoxylin/eosin) where they are identified by their multi-lobed nuclei and characteristic cytoplasmic granules. The second uses flow cytometry, where immune cells can be differentiated by their relative sizes in combination with their different light-scattering properties.

While both such methodologies might be readily available to large medical practices associated with hospitals, and to some well-equipped veterinary clinics, in most cases samples must be sent to diagnostic laboratories resulting in delays to patient treatment. In large-animal veterinary practice in particular, where on-site visits are common practice, rapid detection of neutrophil influx is not available because high-power microscopes are bulky and inconvenient, and histology and examination are time-consuming, while flow cytometers are delicate pieces of equipment that are not suitable for routine relocation from site to site. There is, therefore, a strong need for a rapid (5-10 minutes or less), affordable and portable technology to facilitate the on-site detection of elevated neutrophil levels by either veterinary practitioners (and even farmers) or by smaller human medical practices that do not have the resources to purchase, or access to, sophisticated laboratory equipment.

This application describes an invention aimed at addressing this unmet need and that is of particular utility to the dairy industry. More specifically, the invention is particularly useful in providing early diagnosis of mammary gland infection in cattle and other domesticated mammals (for example, sheep and goats).

Mastitis is a ubiquitous disease caused by the invasion of the mammary gland by bacteria and the subsequent resulting inflammatory response. It is one of the most widespread diseases affecting the dairy industry, leading to annual losses of $2 billion in the US alone[5,6]. Numerous factors contribute to such losses, including: milk production drops; disposal of milk deemed unfit for consumption; cost of drugs, veterinary care and diagnostics; additional labor; and, in rarer cases death of the animal. Losses occur even in the absence of evident disease since milk production drops significantly even the case of subclinical mastitis[7-9].

Earlier diagnosis of mastitic infections can significantly reduce their economic burden and increase efficiency in a number of these areas. Not only does early detection lead to earlier treatment and more rapid resolution, with a concomitant decrease in the risks of serious complications and even death, but also to production savings from both increased yields and a decrease in milk withheld from the market due to adulteration with antibiotics. Furthermore, mastitis in dry cows can have serious clinical consequences for the animal and also results in significant decreases in milk production in subsequent lactations. Thus Dry Cow Therapy (DCT), i.e. prophylactic antibiotic infusion of the udder at drying-off in combination with a teat sealant is a common practice[10,11] that both increases operating costs due to the price of the antibiotics and risks selection of resistant bacterial strains[12,13]. The latter concern could lead to eventual regulation of the prophylactic use of these compounds, as has already occurred with feed, and so anything that would encourage their more prudent use is to be encouraged[14]. In this case, convenient subclinical mastitis tests that could identify infected animals or udder quarters cow-side and so promote more effective selective DCT (sDCT)[15-17] would also yield increased efficiencies for dairy farmers while lowering the costs and resistance risks associated with antibiotic-based prophylaxis.

Mastitis is diagnosed by the appearance of the udder (e.g. redness, temperature, swelling, hardness or pain), and/or by changes in milk appearance (e.g. increased wateriness or appearance of clots, pus or flakes). By this point, however, infection has been firmly established, making the condition more challenging and time-consuming to treat. In addition, milk yields begin to decrease substantially before any clinical symptoms present[18-22], leading to significant economic losses even in such asymptomatic cases, amounting to $1 billion annually in the U.S. alone[23].

Subclinical mastitis can be diagnosed by bacterial culture of aseptically collected milk, though this is both expensive and time consuming. As a result, the prevalence of latent mastitis in both herds and individual animals is most commonly diagnosed using a surrogate marker, the somatic cell count (SCC)[24], since it has been demonstrated that elevated counts are prognostic of bacterial infection[25] and susceptibility to developing clinical symptoms[26].

The utility of SCCs reaches beyond early the treatment of infection, and testing results have additional economic consequences to the farmer. Elevated-SCC milk has a shorter shelf-life and produces lower-quality milk-products[27-31]. It also produces lower yields of milk-derived foodstuffs such as cheese[32]. As a result, many milk distributors offer quality premiums for milk low-SCC milk, further inducing farmers to manage subclinical mastitis in their operations[33]. Our proposed animal-side technology would facilitate earlier detection of mastitis at lower SCCs, making it easier for the dairyman to isolate infected animals and so to capitalize on these incentives.

Furthermore, regulatory authorities set strict limits for maximum allowable counts in milk shipments, with bulk tank SCC (BTSCC) being 750,000 cells/ml in the U.S. and 400,000 in Europe[34], resulting in the wastage of shipments that do not meet these criteria.

Thus, regular SCC testing provides an opportunity for dairy farmers to increase the efficiency of their operations as well as to enhance the well-being of their cattle, and so the development of technologies aimed at improving the sensitivity, reducing the cost, and diminishing the inconvenience of monitoring their herds would be welcomed.

Control of mastitis depends on both a herd and animal-level approach to conducting SCCs[35]. BTSCCs serve to monitor the mastitic state of the entire herd (as well as a quality control point for the milk itself), and increases in BTSCCs can serve as a signal of underlying subclinical mastitis issues. However, due to the dilution of milk from high SCC cows with that of the entire herd, BTSCCs lack sensitivity and so provide a "delayed" warning of a growing problem. As a result, testing of individual animals sampled from the herd is also conducted. This not only facilitates early identification of infected animals but also identifies those contributing to an elevated BTSCC so that they can be isolated and treated.

While alternative approaches, such as measuring the changes in electrical conductivity of milk and measuring the activity of various enzymes, have been proposed or are in use, none possess either the specificity or sensitivity of the SCC[36].

Numerous methods exist for subclinical mastitis diagnosis based on elevated cellular levels in milk. These can be divided into three broad classes: laboratory, on-farm and cow-side methods.

Laboratory methods utilize sophisticated flow cytometry either without or in conjunction with fluorescent staining. Such methods rely on shipment of samples from farms for analysis, which leads to delays between sample collection and receipt of results. A number of commercial devices are available for use in such diagnostic laboratories, including the Fossomatic (Foss) and the Delta SomaScope (Perten Instruments). Farmers using such services typically test once a month and therefore can only track the status of their animals with a temporal resolution of 30 days.

On-farm devices avoid the inconvenience of shipping samples and the associated time delays, and a number of models are available to veterinarians and farmers based on the imaging and computational enumeration of fluorescently labeled cells. These include the Lactoscan SCC (Milkotronic Ltd.), the Nucleocounter SCC (Chemometec) and the QScout (Advanced Animal Diagnostics). These devices are intended to be used in a dedicated laboratory space on the farm, but do not require highly trained operators and can provide same-day test results to the farmer.

Animal-side devices are intended to be used outside of the laboratory setting and provide the benefit of providing SCC information animal-side so that treatment/livestock management decisions can be made immediately. Some of these tests are relatively sophisticated and also rely on the electronic enumeration of fluorescently stained cells, for example, the Cell Counter ICC (DeLaval Inc.) and the Dairy Quality SCC (Dairy Quality). However, older and cruder tests are also available that based on the gelation of somatic cell DNA upon lysis with detergent. These include the California Mastitis Test (CMT)[37,38], where gelation is semi-quantitative and subject to user visual-analog scoring of the degree of milk gelation, and the Wisconsin Mastitis Test (WMT)[39], where the gel is quantified using a graduated scale. These tests are available from numerous vendors, including the Somaticell SCC test (IDEXX).

Two other differentiating factors between these tests are the ability to count all four udder quarters simultaneously, and the ability to differentiate between different milk leukocytes. The former provides enhanced sensitivity not only because the cell count of an affected quarter is not diluted by their non-infected counterparts[40-43], but also because the counts of uninfected quarters can serve as internal negative controls since SCCs vary dramatically from animal to animal and even during lactation[44]. The latter also provides increases sensitivity because the activation and influx of neutrophils occurs very soon after microbial invasion (see below)[45-48]. Numerous researchers have suggested that such differential somatic cell counts (DSCCs) provide an earlier indication of subclinical mastitis than SCCs alone, and the focus of their work has been the detection of elevated levels of neutrophils[49-55].

Of the currently available tests, the CMT provides the ability of test all four udder quarters simultaneously, while the Fossamatic provides the capability of conducting DSCCs and yet these options lie on opposite ends of the portability spectrum. The only user-friendly device currently capable of conducting DSCCs on-farm is the QScout, though it is too bulky to be considered as a truly portable unit and is designed to be used in a dedicated laboratory space.

Furthermore, cost is also a consideration. While the CMT is relatively affordable (inexpensive reagents coupled with reusable hardware) it lacks the sensitivity of direct cell counting and is prone to user subjectivity. SCCs from commercial reference laboratories are relatively inexpensive, but their cost mounts when analyzing four quarters and there is a delay in obtaining results. Animal-side devices use disposal plastic cassettes that cost several dollars per test and cannot analyze all four quarters simultaneously. Finally, the QScout, which can be used by the average farmer, albeit not animal-side, does analyze all four quarters but also uses disposable cassettes which cost approximately $5 per test while the QScout itself costs almost $20,000.

Thus, veterinarians' and farmers' current options regarding SCCs are a trade-off between cost, the convenience of animal-side tests and the sensitivity afforded by laboratory-based methods. In addition to diagnosing other inflammatory conditions in both humans and other animals, this invention addresses the unmet need for a portable and affordable DSCC test that can be used animal-side to provide early diagnosis of subclinical mastitis.

SUMMARY OF THE INVENTION

The purpose of this invention is to provide a rapid (under 10 minute) method to image large numbers of cells (containing neutrophils) and then automatically count the neutrophils without the need for a trained operator or bulky/delicate/expensive equipment.

One difficulty in developing a device to detect neutrophils is the dearth of specifics antigenic cross-species markers for this cell type. Since leukocytes develop along diverging lineages from the same progenitor stem cells, many of their markers are common to more than one group. Without a specific antigen to provide a means to differentiate neutrophils and other cell types, their identification and enumeration are generally limited to the methods described above.

The core of this invention is a method of specifically rendering neutrophils fluorescent and coupling this method to a device capable imaging the cells and counting either the total neutrophils or both the total number of neutrophils and somatic cells in milk or other bodily fluids. Dual-wavelength fluorescence imaging of neutrophils and (optionally) nuclei facilitates DSCC (and optionally also SCC) in a single device and so provides enhanced sensitivity for early infection detection over SCC alone. This invention can also be incorporated into a four-quarter test of udder milk in ruminant animals.

The invention can be portable because it does not contain any of the delicate instrumentation required for flow cytometry nor the bulky optics and motorized stage used in the QScout device[56,57]. The technology allows miniaturization of the optics because it does not need to discriminate between fluorescence intensities nor obtain information on cells sizes to perform differential counts[56], and so can count imaged cells that are only one or two pixels in size, as do current animal-side SCC-only technologies.

This method relies on an enzymatic activity known as chloroacetate esterase (CAE—also known as "specific esterase") that is used to generate a chromophore to identify CAE positive cells[58]. This enzyme is found predominantly in the granules of neutrophils and is used to differentiate them from other granulocytes in traditional histological analysis (by treating samples with a mixture of chromogenic substrates for the enzyme, known as Leder stain).

However, color changes in the visible range provide insufficient contrast to identify specific cells unless viewed under high magnification, which would be incompatible with a portable device and would also require a substantially more sophisticated computer vision algorithm in order to accurately identify neutrophils. This invention utilizes this same enzyme to generate a fluorescent, insoluble product within the neutrophils themselves. As a result, the high-contrast of fluorescence-mode detection means cells can be imaged at much lower magnification (and even de-magnification). This not only reduces the complexity and fragility of the optical system required for imaging, but also reduces the size and weight of the device. Furthermore, by imaging at lower magnification increases the field-of-view and allows for the instantaneous imaging of more cells, thereby increasing the accuracy/precision by increasing the number of countable cells. Finally, and unlike chromogenic histological tests, because the substrates are non-fluorescent while the product is, no separation of staining solution from sample is required prior to imaging.

Esterases are enzymes that catalyze the hydrolysis of ester bonds; different esterases possess different substrate specificities. While the natural substrates and function of CAE are unknown, it has been shown that, with regard to leukocytes, it is present in only neutrophils, mast cells and promyelocytes[59]. This incomplete specificity, however, is not an issue for the purposes of this invention, however, because: (i) it is probable that the promyelocytes that contain CAE belong to the neutrophil lineage; (ii) promyelocytes reside in the bone marrow, since they are still differentiating, and so do not participate in inflammatory processes; and (iii) mast cells are non-migratory and so will not contribute to any increase in cell count during inflammatory processes, therefore allowing one to conclude that any increase in CAE positive cells is due to neutrophil influx.

CAE activity in cells is detected using the substrate naphthol AS-D chloroacetate (NCA), a derivative of 2-naphthol that has been esterified at the hydroxyl by a chloroacetate group (FIG. 1, upper structure). Hydrolysis of this group by CAE releases the free naphthol derivative. In the presence of a diazonium salt, azo-coupling to the aryl alcohol occurs to form an azo compound, and selection of the appropriate diazonium salt produces an insoluble, intense azo dye. A commonly used salt for this purpose is Fast Red TR (FFTR; FIG. 1, lower structure), which results in neutrophils staining a dark red color. In traditional histology, this method is used with a tissue section or blood smear on a glass slide, which is dipped into the reagents, incubated, and then washed prior to examination.

However, this staining still requires a bulky high-magnification microscope to manually identify and enumerate neutrophils, which is tedious, very time consuming and requires specialized training. Automation of counting would require a motorized stage to take multiple photographs for analysis, due to the limited field of view, adding to the cost and complexity of the device, reducing its portability and increasing the assay time due to such data collection restrictions.

Imaging more cells in a single field requires lower power optics (perhaps even less than 1×), which in turn results in a smaller and both a more economical and portable unit. Additional field-of-view and resolving power can be provided, if required, by increasing the resolution of the image sensor without compromising portability. Unfortunately, visible light microscopy is not conducive to reducing magnification indefinitely without significant loss in fidelity because of its limited signal-to-noise ratio. On the other hand, fluorescence microscopy affords the advantage of excellent signal-noise. In fact, several cell-counting devices exist that label cellular nuclei with fluorescent DNA intercalating reagents and produce images for automated enumeration where the "cells" appear as objects only 1-5 pixels in size (e.g., Nucleocounter, Chemometec and Quick SCC, Dairy Quality Inc.; see above and FIG. 2).

This invention is partly based on the fact that some azo dyes are also fluorescent[60]. Furthermore, azo dye precipitates can be formed following enzymatic cleavage from phosphorylated naphthol derivatives that are substrates for phosphatases and appropriate diazonium salt although not all naphthol-based substrates nor diazonium salts produce either colored pigments or intense/specific fluorescence[61-63].

To date, no one has reported the use of fluorescent azo dye products for the detection of esterases, much less than for CAE/neutrophils. Neither has anyone demonstrated that the fluorescence intensity of such products is sufficient to facilitate imaging at low optical magnification, that such fluorescence intensity can be achieved in a practical amount of time (e.g., <10 minutes), nor that there exists sufficient signal-to-noise in such a system to distinguish granulocytes from other cell types.

One aspect of the invention, therefore, involves the incubation of cells with a neutrophil-specific esterase substrate (for example, NCA) and a suitable diazonium salt (for example, Fast Red TR) to produce a fluorescent reaction product, imaging of the cells at sufficient magnification (or demagnification) to facilitate an acceptable compromise between sensitivity (i.e. number of cells imaged) and detectability (i.e. the number of pixels used to image the cells), and quantification of the number of neutrophils using computational image analysis. In one example, cells are imaged at a macro magnification (1×) leading to an image of "cells" of approximately 5 pixels in diameter (assuming a sensor photo site diameter of 2 microns). In another example, cells are de-magnified 2-fold (i.e., magnification of 0.5×) to give "cells" approximately 2-3 pixels in diameter. Regardless of the final magnification, the image is then processed digitally using appropriate approaches (e.g., thresholding or edge detection) to isolate cells from the background of the image and then counted using an appropriate particle counting algorithm.

In another aspect of the invention, cells are incubated with the esterase substrates and with a fluorescent DNA intercalating agent (e.g., DAPI or the Hoechst dyes) with significantly different spectral characteristics, and the cells are imaged and quantitated at different wavelengths to provide metrics for both the total number of cells. In the case of DNA intercalating dyes that are membrane impermeable, additional reagents to facilitate cellular uptake (such as surfactants) may be incorporated. Upon staining, images are taken with a device capable of dual-wavelength illumination and detection in order to produce images of both total cells and neutrophils and so determine the % of neutrophils in the sample. In this case, each image is processed separately to obtain both total and neutrophil counts.

Total cells need not be detected solely using DNA-binding dyes, and other fluorogenic methods for detection of cells or their contents may be used. For example, total cells can be detected by the presence of ubiquitous enzymatic activities such as non-specific esterase using the fluorogenic substrate fluorescein diacetate. In another example, cells can be detected by the uptake of fluorescent dyes by cellular membranes[64].

It has been reported that some CAE detection reagents can penetrate intact cells, but will not necessarily access the CAE (which is present within the lysosomes) unless the neutrophils have been activated, resulting in increased permeability of lysosomal membranes[65]. In one aspect of the invention, therefore, cells are incubated in the absence of membrane disruptors in order to only detect activated neutrophils, while in another aspect a suitable membrane disrupting reagent is included so that all neutrophils can be detected and enumerated.

It should be noted that other systems have been described for the fluorogenic detection of cellular esterase activity, but that these have in general been limited to the detection viable cells or multiple cell populations as opposed to specific cell types[66]. In contrast, this invention focuses on the utilization of a specific esterase activity that is present in a specific subset of clinically relevant cells. More specifically, this invention focuses on CAE, which to date has only been detected optically using standard histological methods. This invention improves on the current art but introducing a high-contrast, low signal-noise fluorescence detection modality for CAE and coupling it to image capture at low magnification to maximize field-of-view, and then to computation image analysis in order to automate and accelerate the acquisition of quantitative data.

In all aspects of the invention, imaging could be of either a section of solid tissue that has been suitably stained or of cells in suspension. Suspended cells could be derived from either bodily fluids or extracted from intact tissue in order produce the suspension.

This invention differs significantly from the traditional CAE histological methods because the reaction solution is not removed from the sample (i.e., by extensive washing). Extensive washing would be incompatible with a test of cells in body fluids without the need to capture cells in some way, for example on a filter, to allow for them to be washed. This additional handing would add to the complexity and time taken for conducting a test and so, by eliminating such handling steps, the speed of the test described here is limited only to the reaction time This, is possible because the reagents are not fluorescent, while the final reaction products (azo dyes) are, and so the signal generated in situ can be detected directly in the sample in real time. As a result, it is important that azo-dye does not form independently of CAE activity, which would result in the generation of a confounding background. As described below, this is not the case under traditional histology conditions.

DESCRIPTIONS OF DRAWINGS

The patent or application file contains at least one drawing executed in color. Copies of this patent or patent application publication with color drawing(s) will be provided by the Office upon request and payment of the necessary fee.

FIG. 1. Structures of naphthol AS-D chloroacetate (A) and Fast Red TR (B).

Figure 2:
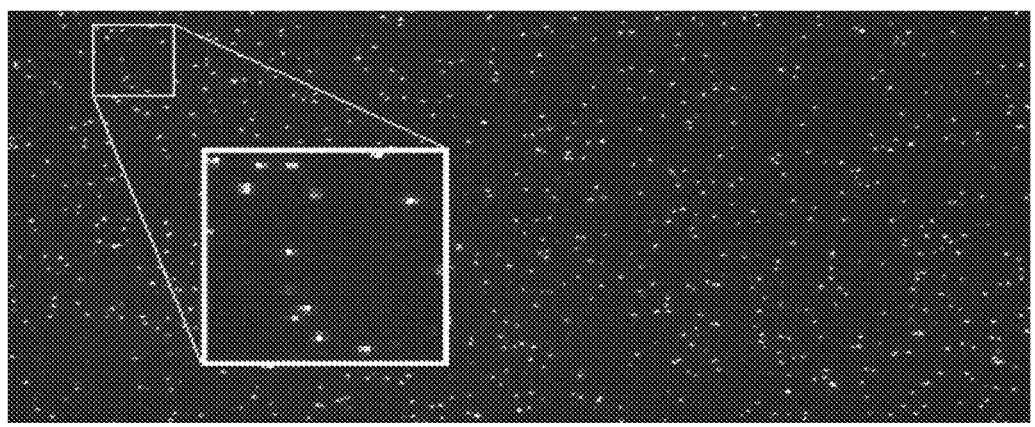

FIG. 2. Example image of bovine somatic cells in milk taken at low magnification following fluorescent labeling. Note the wide field-of-view and that each cell is represented by only 1-4 pixels (inset). This image is reproduced from the documentation for the Nucleocounter SCC.

Figure 3:
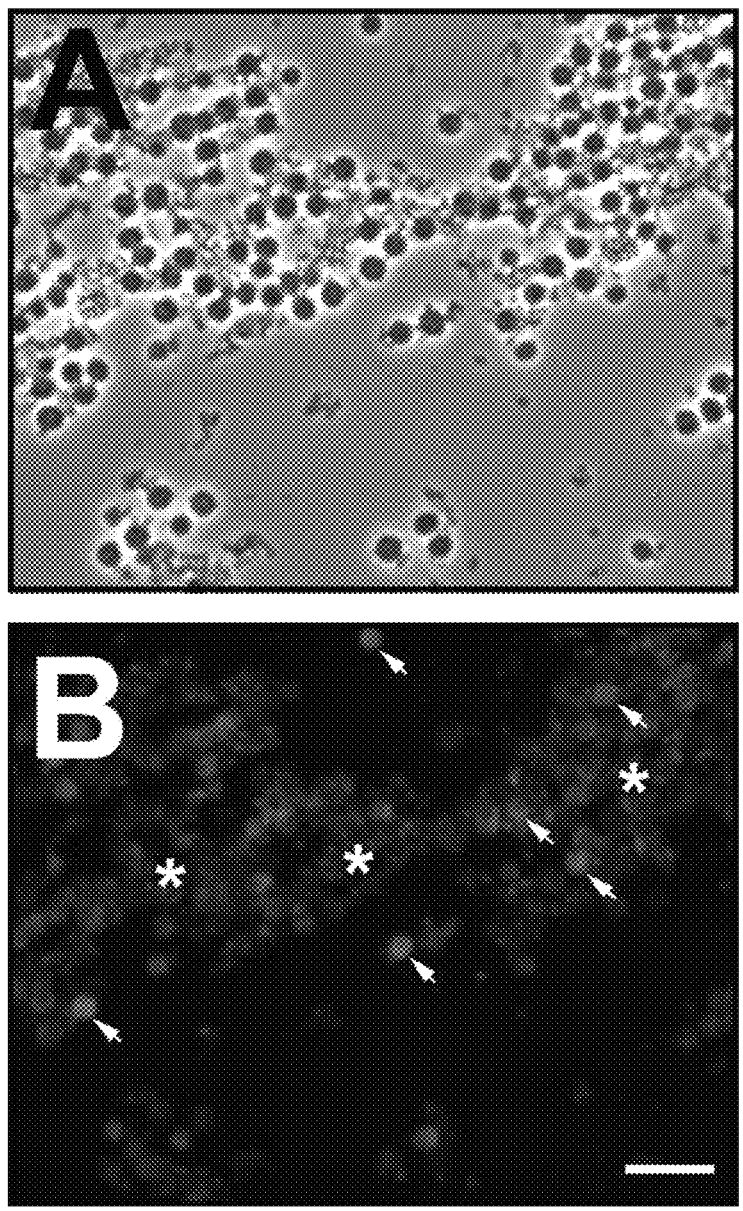

FIG. 3. Fluorescent CAE staining of equine leukocytes. Leukocytes purified from horse blood were stained for CAE and imaged by phase contrast (A) and fluorescence (B) microscopy. Cells were clumped together by an amorphous matrix that itself was fluorescent (asterisks), and that tended to obscure cellular fluorescence, which was nevertheless evident at the peripheries of the clumps (arrows). Bar=25 μm.

Figure 4:
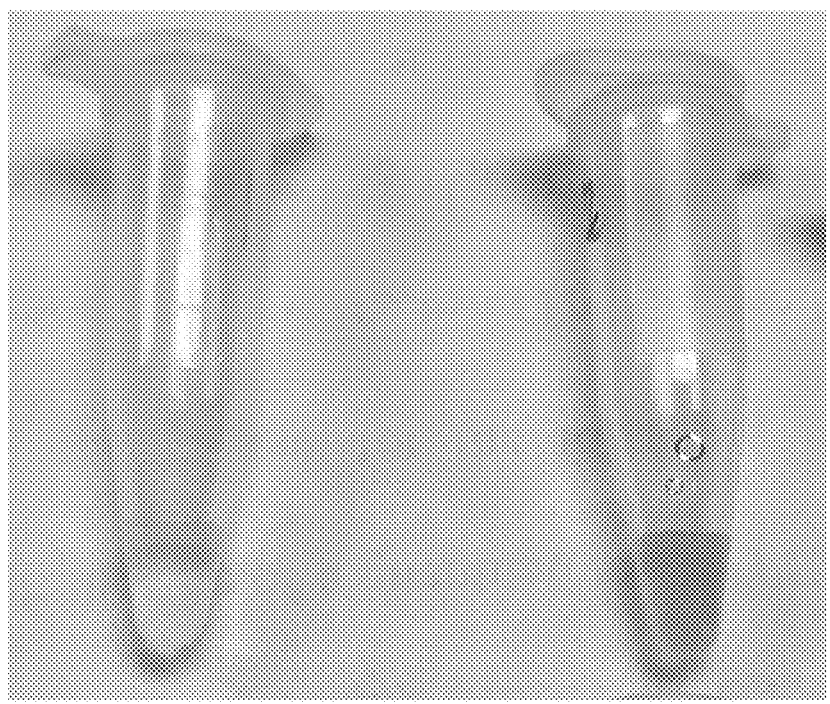

FIG. 4. Effect of PBS on CAE reagent background. CAE reagents were mixed together in the presence of either saline or phosphate buffered saline (PBS). Reactions were photographed 5 minutes after mixing.

Figure 5:
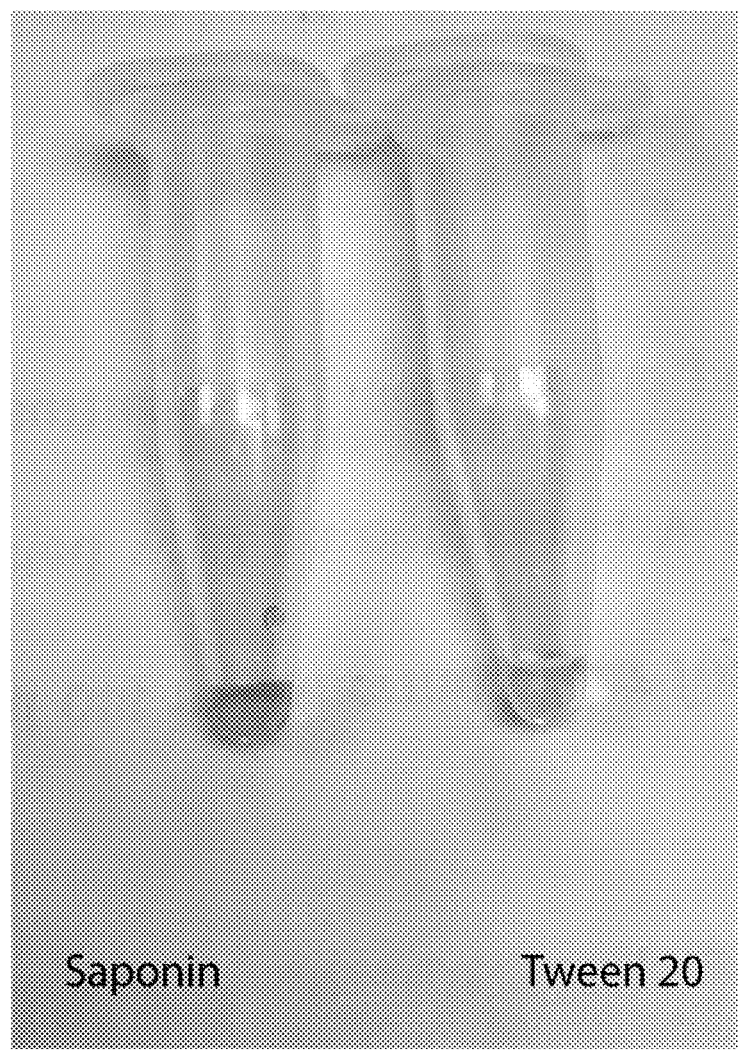

FIG. 5. Effect of surfactants on CAE reagent background. CAE reagents were mixed together in the presence of either 0.05% (w/v) saponin or Tween-20. Reactions were photographed 5 minutes after mixing.

Figure 6:
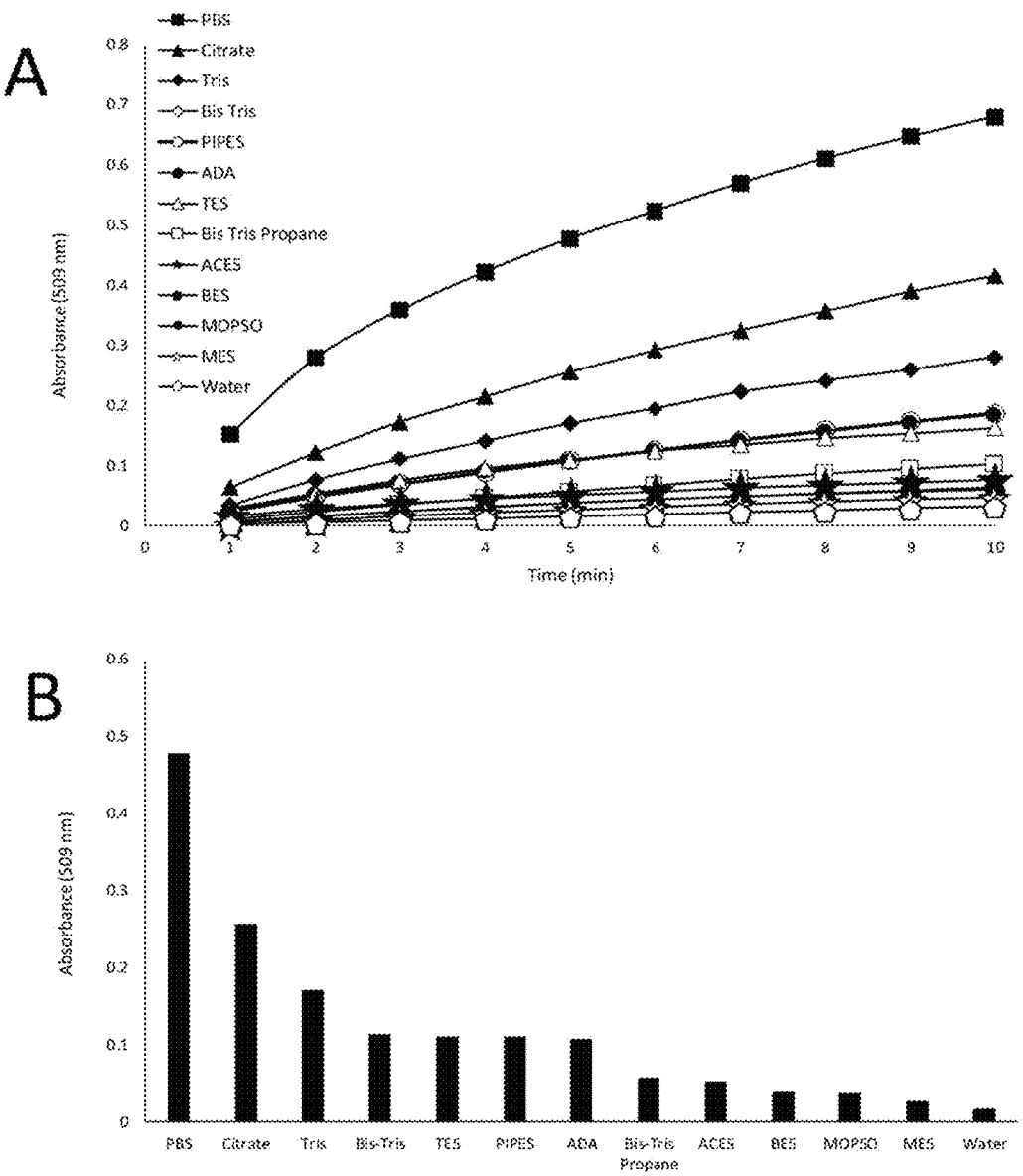

FIG. 6. Effect of buffers on CAE reagent background. CAE reagents were mixed together in the presence of 10 mM of various buffering agents and 20% (v/v) DMSO. Absorbance was read at 509 nm every minute for 10 minutes (A). The absorbance of each sample after 5 minutes is also shown (B).

Figure 7:
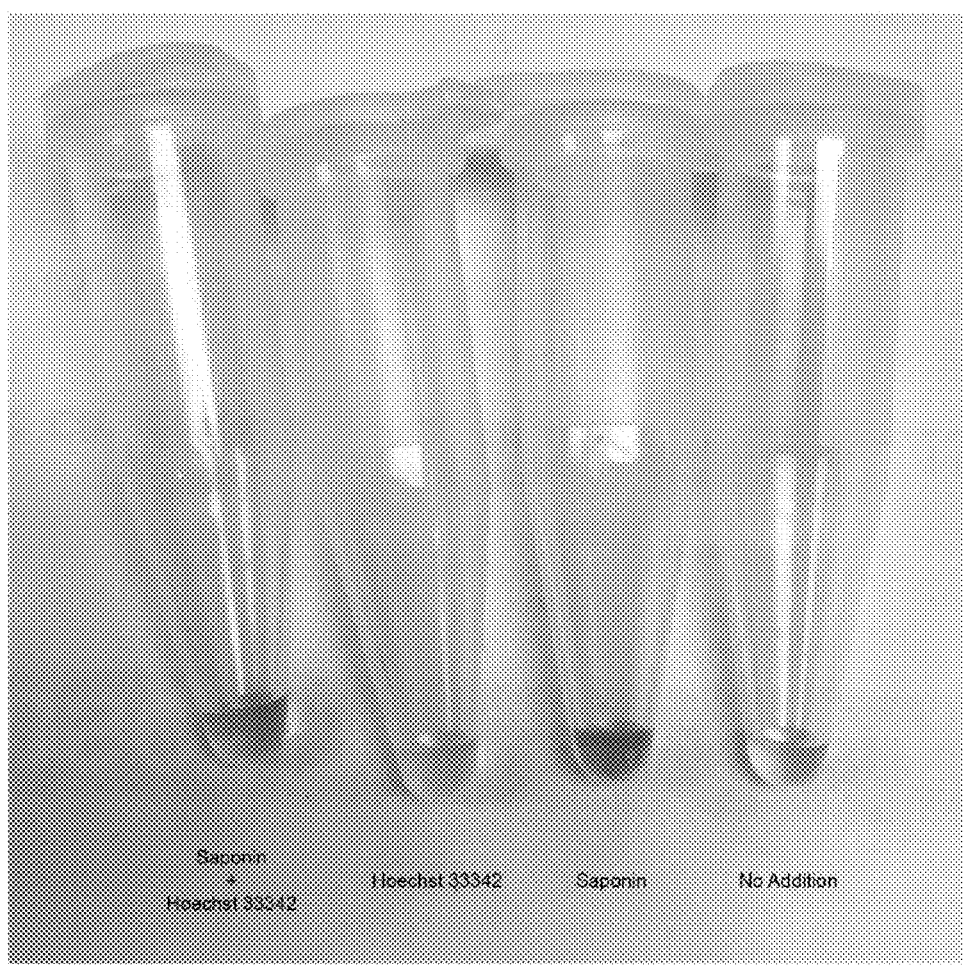

FIG. 7. Effect of saponin and Hoechst 33342 on CAE reagent background. CAE reagents were mixed together in the presence of either 0.05% (w/v) saponin or 25 μg/ml Hoechst 33342, or with a mixture of both or neither. Reactions were photographed 5 minutes after mixing.

Figure 8:
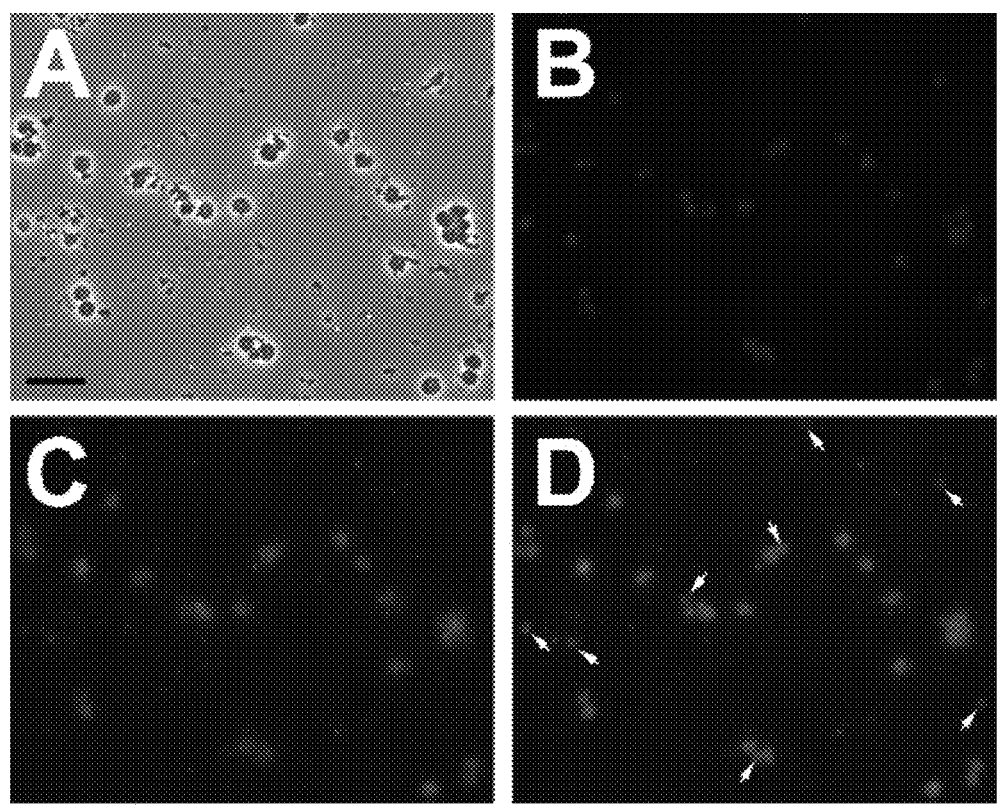

FIG. 8. Specific fluorescence of bovine neutrophils after CAE staining. Cells were stained and imaged by phase contrast (A) and fluorescence microscopy (C-D). Fluorescence was imaged in the DAPI (nuclei; B) and Texas Red (CAE staining; C) channels and images merged to produce a composite (D). Only non-neutrophilic cells were not rendered fluorescent by CAE staining (arrows). Bar=25 μm.

Figure 9:
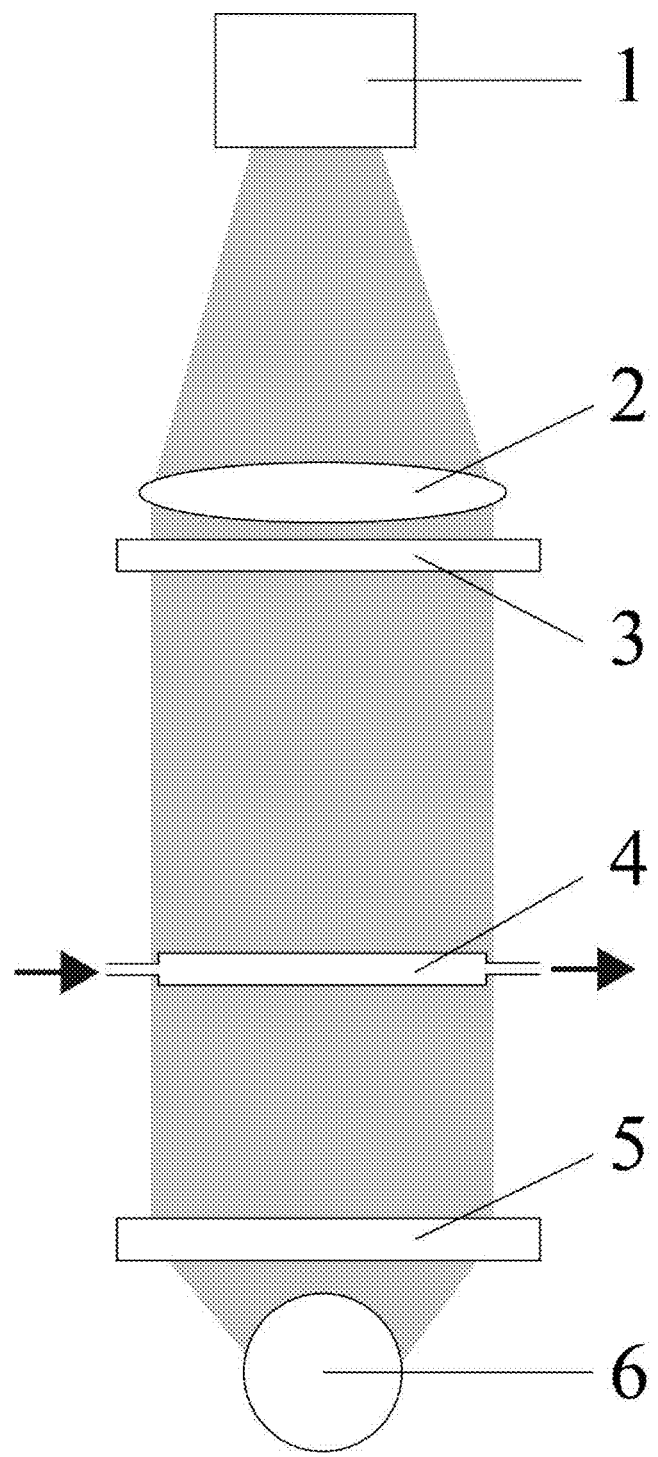

FIG. 9. Schematic representation of an imaging device. (1) Imaging sensor. (2) Lens. (3) Emission Filter. (4) Sample chamber. (5) Excitation filter. (6) Light source. The light path is shown in gray. The arrows indicate flow of sample/reagents in and out of the sample chamber in the case of a reusable system.

DETAILED DESCRIPTION OF THE INVENTION

CAE activity is commonly detected using the Fast Red (FR) series of diazonium salts, though other salts, such as nitrosylated pararosanilin and Fast Corinth V, are used to produce azo dyes of different colors. Furthermore, not all diazonium salts produce azo dyes with the same (or any) fluorescent properties[63]. Any diazonium salt capable of reacting the CAE cleavage product of NCA to generate a fluorescent moiety could be used for the purposes of practicing this invention. Because FRTR has, however, been shown to produce an intensely fluorescent product following reaction a dephosphorylated naphthol phosphate in a phosphatase assay, upon conceiving of the invention, the inventor tested the ability of CAE to render neutrophil cells isolated from equine peripheral blood fluorescent after treatment with a combination with NCA (0.2 mg/ml) and FRTR (2 mg/ml) in a buffer of phosphate buffered saline (PBS).

While this mixture did indeed produce fluorescent material when examined with a fluorescence microscope, the majority of was extracellular and took the form of an aggregated, amorphous mass (FIG. 3). While some cell staining could be detected on the peripheries of the material, the majority of the cells were embedded within it and could not be reliably differentiated from it. As a result, this system, which is commonly used for CAE staining[58,59,65], is clearly unsuitable for the purposes of the present invention because the amorphous material obscures the cells and prevents their detection.

This amorphous material was macroscopically visible and manifested as a pink-red crystalline precipitate. This precipitate also rapidly developed in a solution of PBS containing the same concentrations of NCA and FRTR (FIG. 4). Surprisingly, this material did not develop when NCA and FRTR were incubated in saline alone (FIG. 4), indicating that sodium and potassium chloride were not responsible for the precipitation, but that phosphate ions were.

This was particularly unexpected because PBS is routinely used in CAE histological staining. However, histological procedures afford (and, in this case, require) the extensive washing of slides before specimen examination, since the specimen is affixed to a slide. Thus, any precipitate formed in this context would be removed prior to examination and not even be noticed. This is not an option for tests that are the subject of this invention, since the somatic cells to be imaged are in liquid suspension, rendering the removal of precipitate prior to imaging problematic. Immobilizing the cells on a solid support such as a filter membrane prior to staining to facilitate washing would add substantial time, cost and complexity to the test (due to fixation, filter handling and washing steps and the additional expense of a filter for each test) and would reduce the attractiveness of the test to veterinarians, farmers and physicians.

While cell permeabilization does not appear to be necessary to render cells fluorescent (FIG. 3B, arrows), some nuclear stains are not membrane-permeable and so must be used in conjunction with a detergent or other membrane disrupting reagent if double-staining is required. The surfactant saponin has been shown to increase the CAE activity in neutrophils[65], and so it may also have utility for both purposes in this technology. However, in the absence of buffer but in the presence of 0.05% (w/v) saponin, a mixture of NCA (1 mg/ml) and FRTR (10 mg/ml) in dimethyl sulfoxide (DMSO) turned red within five minutes, while one containing the surfactant Tween-20 at the same concentration did not (FIG. 5). This illustrates that not all reagents are compatible with the concept of this invention, in particular the buffer that is most commonly used in the histological localization of the pertinent enzyme.

In order to test the compatibility of other buffering agents with this system, the author developed a colorimetric assay to measure the development of azo-dye produced by a mixture of NCA and FRTR in the absence of esterase. This assay used NCA and FRTR concentrations of 0.04 mg/ml and 0.4 mg/ml respectively and 20% (v/v) DMSO as a co-solvent to maintain the solubility of the developed azo dye. Using this system, the inventor monitored the production of azo dye product by measuring the optical absorbance of the solution at 509 nm over time. The inventor then tested various commonly used biological buffering agents using this system.

All of the buffering agents produced more color than the sample containing only water and DMSO (FIG. 6A). For clarity, the results at the five-minute time point are shown in FIG. 6B. Phosphate, which is by far the most commonly used buffer used in staining neutrophils for histology, was also by far the worst in promoting the non-enzymatic formation of azo dye. The next worse was citrate, followed by Tris. Interestingly, the Tris is the other buffer that has been used in histologically staining neutrophils[65,67]. The remaining buffers could be broadly classified into two groups: one that produced moderate amounts of azo dye (Bis-Tris, TES, PIPES and ADA) and one that produced low amounts (Bis-Tris propane, ACES, BES, MOPSO and MES). Thus, the two buffers most commonly associated with using NCA as a stain for neutrophils also produce the most background in this system. While, this may not be an issue when conducting histological staining, because of the opportunity afforded to wash away non-specific precipitated dye prior to examination of the sample, this is not an option in the context of the present invention where cells must be stained and detected without any intervening washing steps. Unacceptable levels of background, as produced by, for example, phosphate buffer, prevents reliable detection of neutrophils (FIG. 3). Thus, this test must be conducted either in the absence of a buffer, or in the presence of a buffer that has been empirically determined to be compatible with the system, for example by using the qualitative and quantitative tests described above.

In one aspect of the invention, both neutrophils and total cells are counted. Total cell counting can be achieved by, for example, staining cell nuclei using DNA binding fluorescent probes that fluoresce at a different wavelength to the neutrophil-generated azo dye. However, as demonstrated above, not all chemicals are compatible with this invention and need to be empirically tested for suitability. In this respect, the inventor qualitatively tested the nuclear stain Hoechst 33342 as described above for testing of the surfactant saponin (and using saponin as a positive control). While both the mixture of Hoechst 33342 and saponin and saponin alone both resulted in the generation of the red color characteristic of the azo dye product, neither Hoechst 33342 alone or the absence of either reagent produced a color change (FIG. 7), indicating that Hoechst 33342 is compatible with this system.

By combining these learnings, the inventor then again attempted to stain neutrophils in a leukocyte preparation from equine blood using the same conditions described above, but this time omitting phosphate buffer and including 10 μg/ml Hoechst 33342 to stain nuclei. Furthermore, because Hoechst 33342 is membrane impermeant, 0.05% (w/v) Tween-20 was also included to facilitate access to nuclear DNA.

Under these conditions cells stained well for CAE with no amorphous material forming (FIG. 8). Furthermore, the staining occurred only in neutrophils, which were identifiable by their characteristic lobed nuclei, while other leukocytes did not fluoresce after treatment (FIG. 8D, arrowheads). The exposure time for the nuclei was 200 ms and for the cells was 400 ms, indicating similar levels of fluorescence intensity. Development of CAE fluorescence was rapid and could be observed between the time of reagent mixing, cover-slipping and placement under the microscope.

Because of the similar levels of fluorescence intensity, these neutrophils could be imaged by a device with lower optical power, such as the Nucleocounter SCC, where cells appear as low-pixel-sized dots. While a great number of possible designs could be produced to perform this task, a non-limiting possible schematic configuration is shown in FIG. 9. In this design, a light source (1) illuminates a transparent sample flow cell (3). Depending on the light source, which could, for example, be a white light source, and LED or multiple LEDs, or a laser, an excitation filter (2) could also be employed to control the wavelengths of light that illuminate the sample. The flow cell (3) could either be integrated into the unit and be reusable or could be a single-use unit that is inserted and replaced with each test. Light that passes through the sample then passes though an emission filter (4) that removes the excitatory light but allows the fluorescently-emitted photons to pass through, and then through a focusing lens. The order of the filter and the lens could be interchanged.

After capturing the image on a photosensor (6), the cells, which are represented by either single pixels or clusters of small numbers of pixels, can be counted computationally by a number of different image analysis approaches. For example, cells can be isolated from the background by intensity thresholding to produce a binary bitmap, and the number particles counted. A number of software packages can already perform such computations (e.g. Image J or Open CV). Alternatively, various computer deep-learning approaches could be used to the same effect, of simply the average pixel intensity of the image could be used as a read-out of the cell number. Given the known dimensions/volume of the flow cell, and what portion of it is captured on the sensor, the number of cells in a fixed volume of sample can be computed arithmetically.

The light need not be applied directly through the sample and could be shone perpendicularly to the depicted path either with or without a light guide. Alternatively, an epifluorescence mode could be utilized with the light being shone down directly onto the sample with the fluorescence in the opposite direction to that depicted.

Dual-wavelength image to produce both DSCCs and SCCs can be conducted by using two excitation and emission filters that can be moved into position as required to image the same sample under two lighting conditions. In the case of excitation, two different colored LED or laser light sources could be used either with or without suitable excitation filters.

In the case where the flow cell is reusable, the device could optionally integrate a pumping and valving system to mix the reagent with the sample, inject it into the flow cell and then clean the cell following analysis in preparation for the next sample.

In another embodiment of the invention, the flow cell (be it disposable or reusable) contains four separate compartments that are imaged simultaneously to count neutrophils in four separate samples. This embodiment is of particular utility for counting cells in milk obtained from four udder quarters from a single ruminant animal and could be used for both SCCs and DSCCs determination.

The sample could be a bodily fluid that is applied directly to the device (e.g., milk or synovial fluid) or could be first processes prior to use. For example, erythrocytes in blood samples could first be lysed using ammonium chloride to render the sample less opaque, or leukocytes could first be purified from the sample by, for example, density centrifugation. Alternatively, samples could be filters prior to treatment and imaging in order to remove large particulates.

REFERENCES

1 Butterfield, T. A., Best, T. M. & Merrick, M. A. The dual roles of neutrophils and macrophages in inflammation: a critical balance between tissue damage and repair. *J Athl Train* 41, 457-465 (2006).

2 Wright, H. L., Moots, R. J., Bucknall, R. C. & Edwards, S. W. Neutrophil function in inflammation and inflammatory diseases. *Rheumatology (Oxford)* 49, 1618-1631, doi:10.1093/rheumatology/keq045 (2010).

3 Kelly, A. L., Tiernan, D., O'Sullivan, C. & Joyce, P. Correlation between bovine milk somatic cell count and polymorphonuclear leukocyte level for samples of bulk milk and milk from individual cows. *J Dairy Sci* 83, 300-304, doi:10.3168/jds.S0022-0302(00)74878-8 (2000).

4 Brazil, T. J. et al. Kinetics of pulmonary neutrophil recruitment and clearance in a natural and spontaneously resolving model of airway inflammation. *Clin Exp Allergy* 35, 854-865, doi:10.1111/j.1365-2222.2005.02231.x (2005).

5 Petrovski, K. R., Trajcev, M. & Buneski, G. A review of the factors affecting the costs of bovine mastitis. *J S Aft Vet Assoc* 77, 52-60 (2006).

6 Halasa, T., Huijps, K., Osteras, O. & Hogeveen, H. Economic effects of bovine mastitis and mastitis management: a review. *Vet Q* 29, 18-31, doi:10.1080/01652176.2007.9695224 (2007).

7 Halasa, T. et al. Production loss due to new subclinical mastitis in Dutch dairy cows estimated with a test-day model. *J Dairy Sci* 92, 599-606, doi:10.3168/jds.2008-1564 (2009).

8 Mungube, E. O. et al. Reduced milk production in udder quarters with subclinical mastitis and associated economic losses in crossbred dairy cows in Ethiopia. *Trop Anim Health Prod* 37, 503-512 (2005).

9 Bradley, A. Bovine mastitis: an evolving disease. *Vet J* 164, 116-128 (2002).

10 Arnold, M. & Bewley, J. *Management of the Dry Cow to Prevent Mastitis*. (University of Kentucky, 2012).

11 Parker, K. I., Compton, C. W., Anniss, F. M., Heuer, C. & McDougall, S. Quarter-level analysis of subclinical and clinical mastitis in primiparous heifers following the use of a teat sealant or an injectable antibiotic, or both, precalving. *J Dairy Sci* 91, 169-181, doi:10.3168/jds.2007-0212 (2008).

12 Kromker, V. & Leimbach, S. Mastitis treatment-Reduction in antibiotic usage in dairy cows. *Reprod Domest Anim* 52 Suppl 3, 21-29, doi:10.1111/rda.13032 (2017).

13 Berghash, S. R., Davidson, J. N., Armstrong, J. C. & Dunny, G. M. Effects of antibiotic treatment of nonlactating dairy cows on antibiotic resistance patterns of bovine mastitis pathogens. *Antimicrob Agents Chemother* 24, 771-776 (1983).

14 Oliver, S. P. & Murinda, S. E. Antimicrobial resistance of mastitis pathogens. *Vet Clin North Am Food Anim Pract* 28, 165-185, doi:10.1016/j.cvfa.2012.03.005 (2012).

15 Rindsig, R. B., Rodewald, R. G., Smith, A. R. & Spahr, S. L. Complete versus selective dry cow therapy for mastitis control. *J Dairy Sci* 61, 1483-1497, doi:10.3168/jds.S0022-0302(78)83753-9 (1978).

16 Osteras, O., Edge, V. L. & Martin, S. W. Determinants of success or failure in the elimination of major mastitis pathogens in selective dry cow therapy. *J Dairy Sci* 82, 1221-1231, doi:10.3168/jds.S0022-0302(99)75345-2 (1999).

17 Edmondson, P. in *Veterinary Practice* Vol. 47 46-50 (2015).

18 Hagnestam-Nielsen, C., Emanuelson, U., Berglund, B. & Strandberg, E. Relationship between somatic cell count and milk yield in different stages of lactation. *J Dairy Sci* 92, 3124-3133, doi:10.3168/jds.2008-1719 (2009).

19 Koldeweij, E., Emanuelson, U. & Janson, L. Relation of milk production loss to milk somatic cell count. *Acta Vet Scand* 40, 47-56 (1999).

20 Cinar, M., Serbester, U., Ceyhan, A. & Gorgulu, M. Effect of somatic cell count on milk yield and composition of first and second lactation dairy cow. *Ital J Anim Sci* 14, 105-108 (2015).

21 Hortet, P. & Seegers, H. Calculated milk production losses associated with elevated somatic cell counts in dairy cows: review and critical discussion. *Vet Res* 29, 497-510 (1998).

22 O'Brien, B., Gallagher, B., Joyce, P., Meaney, W. J. & Kelley, A. in 54*th EAAP Annual Meeting* (EAAP, Bled, Slovenia, 2004).

23 Ott, S. in *Proceedings of the 38th annual meeting of National Mastitis Council,* 152-156.

24 Schukken, Y. H., Wilson, D. J., Welcome, F., Garrison-Tikofsky, L. & Gonzalez, R. N. Monitoring udder health and milk quality using somatic cell counts. *Vet Res* 34, 579-596, doi:10.1051/vetres:2003028 (2003).

25 Schwarz, D. et al. Somatic cell counts and bacteriological status in quarter foremilk samples of cows in Hesse, Germany—a longitudinal study. *J Dairy Sci* 93, 5716-5728, doi:10.3168/jds.2010-3223 (2010).

26 Beaudeau, F., Seegers, H., Fourichon, C. & Hortet, P. Association between milk somatic cell counts up to 400,000 cells/ml and clinical mastitis in French Holstein cows. *Vet Rec* 143, 685-687 (1998).

27 Geary, U., Lopez-Villalobos, N., O'Brien, B., Garrick, D. J. & Shalloo, L. Estimating the impact of somatic cell count on the value of milk utilising parameters obtained from the published literature. *J Dairy Res* 81, 223-232, doi:10.1017/S0022029914000053 (2014).

28 Geary, U., Lopez-Villalobos, N., O'Brien, B., Garrick, D. J. & Shalloo, L. Meta-analysis to investigate relationships between somatic cell count and raw milk composition, Cheddar cheese processing characteristics and cheese composition. *Irish J Agr Food Res* 52, 119-133 (2013).

29 Mazal, G., Vianna, P. C., Santos, M. V. & Gigante, M. L. Effect of somatic cell count on Prato cheese composition. *J Dairy Sci* 90, 630-636, doi:10.3168/jds.S0022-0302(07)71545-X (2007).

30 Ma, Y. et al. Effects of somatic cell count on quality and shelf-life of pasteurized fluid milk. *J Dairy Sci* 83, 264-274, doi:10.3168/jds.S0022-0302(00)74873-9 (2000).

31 Li, N., Richoux, R., Boutinaud, M., Martin, P. & Gagnaire, V. Role of somatic cells on dairy processes and products: a review. *Dairy Sci Technol* 94, 517-538, doi:10.1007/s13594-014-0176-3 (2014).

32 Barbano, D. M., Rasmussen, R. R. & Lynch, J. M. Influence of Milk Somatic Cell Count and Milk Age on Cheese Yield. *J Dairy Sci* 74, 369-388 (1991).

33 Looper, M. Reducing Somatic Cell Count in Dairy Cattle. University of Arkansas FSA4002, 1-4.

34 APHIS. *Determining U.S. milk quality using bulk-tank somatic cell counts,* 2011 (USDA, 2012).

35 Barkema, H. W., De Vliegher, S., Piepers, S. & Zadoks, R. N. Herd level approach to high bulk milk somatic cell count problems in dairy cattle. *Vet Q* 33, 82-93, doi:10.1080/01652176.2013.799791 (2013).

36 Lam, T., Olde Riekerink, R., Sampimon, O. & Smith, H. Mastitis diagnostics and performance monitoring: a practical approach. *Ir Vet J* 62 Suppl 4, S34-39, doi:10.1186/2046-0481-62-S4-S34 (2009).

37 Dingwell, R. T., Leslie, K. E., Schukken, Y. H., Sargeant, J. M. & Timms, L. L. Evaluation of the California mastitis test to detect an intramammary infection with a major pathogen in early lactation dairy cows. *Can Vet J* 44, 413-415 (2003).

38 Barnum, D. A. & Newbould, F. H. The Use of the California Mastitis Test for the Detection Of Bovine Mastitis. *Can Vet J* 2, 83-90 (1961).

39 Bodoh, G. W., Pearson, R. E., Schultze, W. D. & Miller, R. H. Variation in Wisconsin Mastitis Test Scores of bucket milk samples and relationship to bacterial infections. *J Dairy Sci* 64, 123-129, doi:10.3168/jds.S0022-0302(81)82536-2 (1981).

40 Thurmond, M. C. A method to estimate the somatic cell count of milk from a mastitic quarter using composite somatic cell count. *Can J Vet Res* 54, 190-194 (1990).

41 Berglund, I., Pettersson, G., Ostensson, K. & Svennersten-Sjaunja, K. Quarter milking for improved detection of increased SCC. *Reprod Domest Anim* 42, 427-432, doi:10.1111/j.1439-0531.2006.00803.x (2007).

42 Mollenhorst, H., van der Tol, P. P. & Hogeveen, H. Somatic cell count assessment at the quarter or cow milking level. *J Dairy Sci* 93, 3358-3364, doi:10.3168/jds.2009-2842 (2010).

43 Dohoo, I. R. & Meek, A. H. Somatic cell counts in bovine milk. *Can Vet J* 23, 119-125 (1982).

44 Sharma, N., Singh, N. K. & Bhanwal, M. S. Relationship of Somatic Cell Count and Mastitis: An Overview. *Asian-Aust J Anim Sci* 24, 429-438 (2011).

45 Paape, M. J., Lilius, E. M., Wiitanen, P. A., Kontio, M. P. & Miller, R. H. Intramammary defense against infections induced by *Escherichia coli* in cows. *Am J Vet Res* 57, 477-482 (1996).

46 Paape, M., Mehrzad, J., Zhao, X., Detilleux, J. & Burvenich, C. Defense of the bovine mammary gland by polymorphonuclear neutrophil leukocytes. *J Mammary Gland Biol Neoplasia* 7, 109-121 (2002).

47 Rivas, A. L., Quimby, F. W., Blue, J. & Coksaygan, O. Longitudinal evaluation of bovine mammary gland health status by somatic cell counting, flow cytometry, and cytology. *J Vet Diagn Invest* 13, 399-407, doi:10.1177/104063870101300506 (2001).

48 Mehrzad, J., Duchateau, L. & Burvenich, C. Viability of milk neutrophils and severity of bovine coliform mastitis. *J Dairy Sci* 87, 4150-4162, doi:10.3168/jds.S0022-0302(04)73558-4 (2004).

49 Pillai, S. R., Kunze, E., Sordillo, L. M. & Jayarao, B. M. Application of differential inflammatory cell count as a tool to monitor udder health. *J Dairy Sci* 84, 1413-1420, doi:10.3168/jds.S0022-0302(01)70173-7 (2001).

50 Alhussien, M. et al. A comparative study on the blood and milk cell counts of healthy, subclinical, and clinical mastitis Karan Fries cows. *Vet World* 8, 685-689, doi:10.14202/vetworld.2015.685-689 (2015).

51 Alhussien, M. et al. Incidence of mastitis and activity of milk neutrophils in Tharparkar cows reared under semi-arid conditions. *Trop Anim Health Prod* 48, 1291-1295, doi:10.1007/s11250-016-1068-8 (2016).

52 Schwarz, D. et al. Flow cytometric differential cell counts in milk for the evaluation of inflammatory reactions in clinically healthy and subclinically infected bovine mammary glands. *J Dairy Sci* 94, 5033-5044, doi:10.3168/jds.2011-4348 (2011).

53 Swain, D. K., Kushwah, M. S., Kaur, M. & Dang, A. K. Neutrophil dynamics in the blood and milk of crossbred cows naturally infected with *Staphylococcus aureus*. *Vet World* 8, 336-345, doi:10.14202/vetworld.2015.336-345 (2015).

54 Dosogne, H., Vangroenweghe, F., Mehrzad, J., Massart-Leen, A. M. & Burvenich, C. Differential leukocyte count method for bovine low somatic cell count milk. *J Dairy Sci* 86, 828-834, doi:10.3168/jds.S0022-0302(03)73665-0 (2003).
55 Schwarz, D. et al. Microscopic differential cell counts in milk for the evaluation of inflammatory reactions in clinically healthy and subclinically infected bovine mammary glands. *J Dairy Res* 78, 448-455, doi:10.1017/S0022029911000574 (2011).
56 Wardlaw, S. C., Levine, R. A. & Rodriguez, R. R. Determination of white blood cell differential and reticulocyte counts. U.S. Pat. No. 6,350,613 (2002).
57 Goncalves, J. L. et al. Using milk leukocyte differentials for diagnosis of subclinical bovine mastitis. *J Dairy Res* 84, 309-317, doi:10.1017/S0022029917000267 (2017).
58 Kashima, T. G., Inagaki, Y., Grammatopoulos, G. & Athanasou, N. A. Use of chloroacetate esterase staining for the histological diagnosis of prosthetic joint infection. *Virchows Arch* 466, 595-601, doi:10.1007/s00428-015-1722-y (2015).
59 Yam, L. T., Li, C. Y. & Crosby, W. H. Cytochemical identification of monocytes and granulocytes. *Am J Clin Pathol* 55, 283-290 (1971).
60 Jaggi, N., Giri, M. & Yadav, K. Absorption and fluorescence spectraof disperse red 19—An azo dye. *Ind J Pure Appl. Phys* 51, 883-836 (2013).
61 Dolbeare, F., Vanderlaan, M. & Phares, W. Alkaline phosphatase and an acid arylamidase as marker enzymes for normal and transformed WI-38 cells. *J Histochem Cytochem* 28, 419-426, doi:10.1177/28.5.6247391 (1980).
62 Tsuchiya, T., Matsumoto, Y. & Kurihara, S. The fluorescent simultaneous azo dye technique for demonstration of tartrate-resistant acid phosphatase (TRAP) activity in osteoclast-like multinucleate cells. *J Bone Miner Metab* 13, 71-76 (1995).
63 Ziomek, C. A., Lepire, M. L. & Torres, I. A highly fluorescent simultaneous azo dye technique for demonstration of nonspecific alkaline phosphatase activity. *J Histochem Cytochem* 38, 437-442, doi:10.1177/38.3.1689343 (1990).
64 Baumgart, T., Hunt, G., Farkas, E. R., Webb, W. W. & Feigenson, G. W. Fluorescence probe partitioning between Lo/Ld phases in lipid membranes. *Biochim Biophys Acta* 1768, 2182-2194, doi:10.1016/j.bbamem.2007.05.012 (2007).
65 Wozniak, J. T., Orchard, T. L., Mackie, P. H., Mistry, D. K. & Stuart, J. Lysosomal enzyme cytochemistry of blood neutrophils. *J Clin Pathol* 31, 648-653 (1978).
66 Redelma, D. D. Fluorescent dyes for identification and enumerarion of viable cells in milk. (1992).
67 Sigma-Aldrich, Inc. NAPHTHOL AS-D CHLOROACETATE ESTERASE AND α-NAPHTHYL ACETATE ESTERASE (Procedure No. 90). (2018).

The invention claimed is:
1. A method for detecting neutrophils in a bodily fluid comprising:
   contacting the fluid with naphthol AS-D chloroacetate (NCA) and a diazonium salt that can form a fluorescent azo dye upon reaction with de-esterified NCA in the absence of a buffering agent or in the presence of a buffering agent that does not promote the formation of a fluorescent precipitate or azo dye from NCA and the diazonium salt to form a mixture;
   incubating the mixture;
   imaging the mixture with a fluorescence imaging device;
   processing the image to count the number of cells stained with the fluorescent azo dye;
   and calculating the number of neutrophils per unit volume in the bodily fluid.
2. The method of claim 1 where the method comprises contacting the bodily fluid with a buffering agent that does not promote the formation of a fluorescent precipitate or azo dye from NCA and the diazonium salt.
3. The method of claim 2 where the buffering agent is chosen from: Bis-Tris, TES, PIPES, ADA, Bis-Tris propane, ACES, BES, MOPSO or MES.
4. The method of claim 1, wherein the mixture further comprises a surfactant.
5. The method of claim 4 where the surfactant is Tween-20.
6. The method of claim 1 further comprising using a non-specific fluorescent cell stain whose spectral properties differ from the fluorescent azo dye.
7. The method of claim 6 where the non-specific fluorescent cell stain is a DNA-binding fluorophore.
8. The method of claim 1 where the NCA is a chromogenic esterase substrate.
9. The method of claim 6 where cells stained with the fluorescent azo dye and cells stained with the non-specific fluorescent cell stain are counted separately.
10. The method of claim 1 where the bodily fluid is milk.
11. The method of claim 10 where the fluorescence imaging device simultaneously images milk samples derived from four udder quarters from a single ruminant to produce four individual differential somatic cell counts.
12. The method of claim 11 further comprising using a non-specific fluorescent cell stain whose spectral properties differ from the fluorescent azo dye.
13. The method of claim 12 where the non-specific fluorescent cell stain is a DNA-binding fluorophore.
14. The method of claim 11 where the NCA is a chromogenic esterase substrate.
15. The method of claim 12 where cells stained with the fluorescent azo dye and cells stained with the non-specific fluorescent cell stain are counted separately.
16. The method of claim 12 where only the non-specific fluorescent cell stain is used to produce four somatic cell counts.

* * * * *